United States Patent
Ishikawa

(10) Patent No.: US 8,044,357 B2
(45) Date of Patent: Oct. 25, 2011

(54) RADIATION DOSIMETER AND RADIATION DOSE COMPUTING PROGRAM

(75) Inventor: Masayori Ishikawa, Sapporo (JP)

(73) Assignee: National University Corporation Hokkaido University (JP)

( * ) Notice: Subject to any disclaimer, the term of this patent is extended or adjusted under 35 U.S.C. 154(b) by 420 days.

(21) Appl. No.: 12/443,101

(22) PCT Filed: Sep. 26, 2007

(86) PCT No.: PCT/JP2007/068675
§ 371 (c)(1),
(2), (4) Date: Mar. 26, 2009

(87) PCT Pub. No.: WO2008/038662
PCT Pub. Date: Apr. 3, 2008

(65) Prior Publication Data
US 2010/0038547 A1    Feb. 18, 2010

(30) Foreign Application Priority Data
Sep. 26, 2006   (JP) .................................. 2006-261241

(51) Int. Cl.
*G01T 1/20*    (2006.01)
(52) U.S. Cl. ......................................................... 250/369
(58) Field of Classification Search .............. 250/361 R, 250/369; 378/65
See application file for complete search history.

(56) References Cited

U.S. PATENT DOCUMENTS

| | | | |
|---|---|---|---|
| 6,320,935 B1 * | 11/2001 | Shinar et al. | 378/119 |
| 2004/0034269 A1 * | 2/2004 | Ozaki | 600/1 |
| 2004/0238749 A1 | 12/2004 | Fontbonne et al. | |

FOREIGN PATENT DOCUMENTS

| | | |
|---|---|---|
| JP | 2001-56381 A | 2/2001 |
| JP | 2003-194953 A | 7/2003 |
| JP | 2004-191327 A | 7/2004 |
| JP | 2004-526155 A | 8/2004 |
| WO | 2005/008287 A1 | 1/2005 |

OTHER PUBLICATIONS

International Search Report for International Application No. PCT/JP2007/068675; Date of mailing Nov. 20, 2007; with English translation.

* cited by examiner

*Primary Examiner* — David Porta
*Assistant Examiner* — Marcus Taningco
(74) *Attorney, Agent, or Firm* — Cantor Colburn LLP

(57) ABSTRACT

Light emitted in correspondence to ionizing radiation incident from a scintillator is fed through an optical fiber to a photoelectron multiplier tube by which it is converted to an electrical signal. The electrical signal is amplified by a signal amplifying circuit, and any light emission events of given or higher intensity are discriminated by a discriminator and counted by a counter. The count value is fed to a computer. The computer converts the count value to a dosage on the basis of an exponential relationship lying between the light emission intensity and the number of emission events, thereby attaining detection of the dosage.

13 Claims, 6 Drawing Sheets

RADIATION DOSIMETER AND RADIATION DOSE COMPUTING PROGRAM

CROSS REFERENCE TO RELATED APPLICATIONS

This is a U.S. national stage of application No. PCT/JP2007/068675 filed on 26 Sep. 2007. Priority under 35 U.S.C. §119(a) and 35 U.S.C. §365(b) is claimed from Japanese Application No. 2006-261241 filed Sep. 26, 2006, the disclosure of which is also incorporated herein by reference.

TECHNICAL FIELD

The present invention relates to detection of ionizing radiation dosage using a scintillator.

BACKGROUND ART

In the field of radiotherapy, an ionization chamber is generally used for measuring ionizing radiation. An ionization chamber is a measuring device which collects charges, generated at the time of ionization of air contained in a minute volume by radiation, by means of a high voltage of several hundreds of volts, and assesses a dosage from an amount of charges which are collected.

On the other hand, solid-state detectors are also used as a means for measuring the dosage. JP 2004-526155 A, for example, discloses a detector formed by a combination of a scintillator and an optical fiber, in which the scintillator emits light by an ionization action of radiation. The detector then measures the amount of light emission to thereby assess the dosage, based on a proportional relationship between the amount of light emission and the ionization. Here, a photoelectron multiplier tube is used for measurement of the amount of light emission, which is then converted to electric current.

Further, WO 2005/008287 A discloses technology related to counting of thermal neutron flux using a scintillator.

In JP 2004-526155 A described above, when the amount of electric current which is converted from the amount of light emission is extremely small, it is necessary to take measures such as (i) increasing the amount of light emission; (ii) increasing the amplification factor after conversion of electric current; (iii) employing a high-precision ammeter; and so on.

While the measures for increasing the amount of light emission (above (i)) can be achieved by increasing the size of the scintillator, a large size scintillator is disadvantageous in measurement in a very small region. Further, the above measures (ii) and (iii) would require expensive electrical equipment.

DISCLOSURE OF THE INVENTION

A radiation dosimeter according to the present invention includes a scintillator which emits light by incident ionizing radiation, a photoelectric converter which converts light, which is output from the scintillator, to an electric current, a counter which counts the number of events, concerning an output from the photoelectric converter, having an intensity which is a predetermined threshold value or greater, and a dosage computing unit which converts a count value obtained by the counter to a dosage to obtain the dosage, based on a relationship in which a frequency of occurrence of each event exponentially decreases as the intensity of light of the event increases.

Also, the present invention relates to a program for detecting the above-described dosage by a computer, and to a medium in which the program is recorded.

According to the present invention, the number of events of light emission from a scintillator, which is substantially free from light emission caused by a photoelectric effect within the scintillator due to ionizing radiation, occurring with the light emission intensity exceeding a predetermined threshold value, is counted and converted to dosage. It is therefore possible to detect an ionizing radiation dosage in a wide range by utilizing a relatively small scintillator and a relatively simple circuit.

BRIEF DESCRIPTION OF THE DRAWINGS

These and other objects of the invention will be explained in the description below, in connection with the accompanying drawings, in which.

BEST MODE FOR CARRYING OUT THE INVENTION

Preferred embodiments of the present invention will be described with reference to the drawings.

Figure 1:
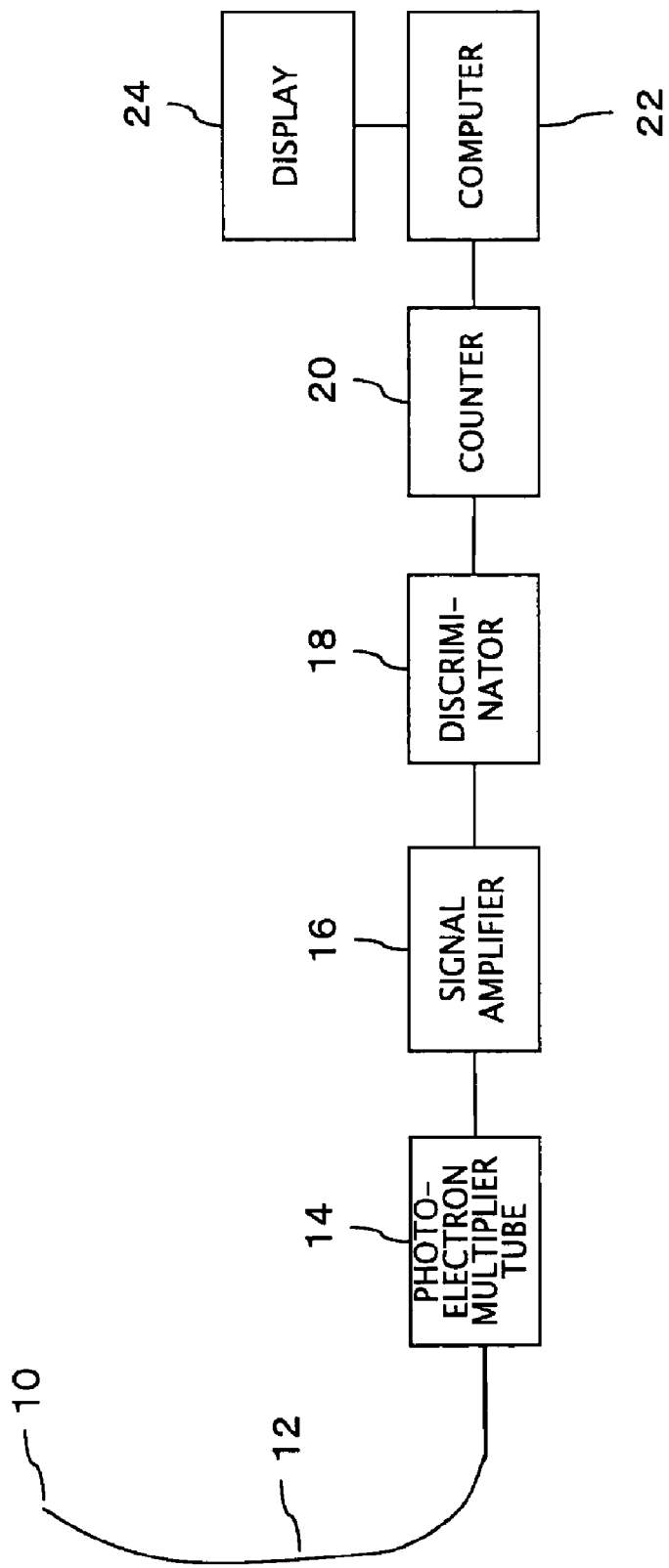
FIG. 1 is a diagram illustrating a structure of a radiation dosimeter according to an embodiment of the present invention.

FIG. 1 is a diagram illustrating a structure of a radiation dosimeter according to an embodiment of the present invention. This radiation dosimeter measures a dosage during radiotherapy performed using X-rays and γ-rays.

A scintillator 10, which is formed from a plastic scintillator, for example, converts ionizing radiation to light. According to this embodiment, as a large amount of light is not required, the scintillator 10 can be formed to have a small size of approximately 1 mm φ×0.1 mm, for example. Compared to the conventional example in which a scintillator having a size of 1 mm φ×10 mm is used, the size of the scintillator 10 in the present embodiment is approximately a hundredth, which results in an increase in the spatial of 100 times. Further, when a plurality of scintillators 10 are provided, it is possible to detect an ionizing radiation dose at a plurality of positions.

Here, in the present embodiment, an organic scintillator, and particularly a plastic scintillator, is adopted as the scintillator 10, so that the ionizing radiation is converted to light with substantially no light emission occurring due to a photoelectric effect within the substance by means of the ionizing radiation.

It should be noted that with the use of a scintillator containing a light element as a major component, similarly, substantially no light emission is caused by a photoelectric effect within the substance due to the ionizing radiation, as in the case of the plastic scintillator. Particularly, a scintillator containing a light element as a major component, whose emission delay time is 10 nanoseconds or less, is known, and the use of such a scintillator enables reliable separation of events and accurate counting of events.

Further, it is possible to employ a scintillator formed of organic and inorganic layered perovskite type compounds, expressed by a general formula $(C_nH_{2n+1}NH_3)2pX_4$ (wherein X is halogen, n=3 to 10). This substance forms a multiple quantum well structure including an organic layer formed of alkylamine as a barrier layer and an inorganic layer formed of lead halide as a well layer. Excitons confined in the well layer of this substance emit light by irradiation with radiation. Further, a scintillator material, $Li_2O$—$B_2O_3$:$Ce^{3+}$, is also known for a scintillator for neutrons. As with the plastic scintillator, these scintillators are also capable of converting ionizing radiation to light with substantially no light emission caused by a photoelectric effect within the substances due to the ionizing radiation.

Figure 2:
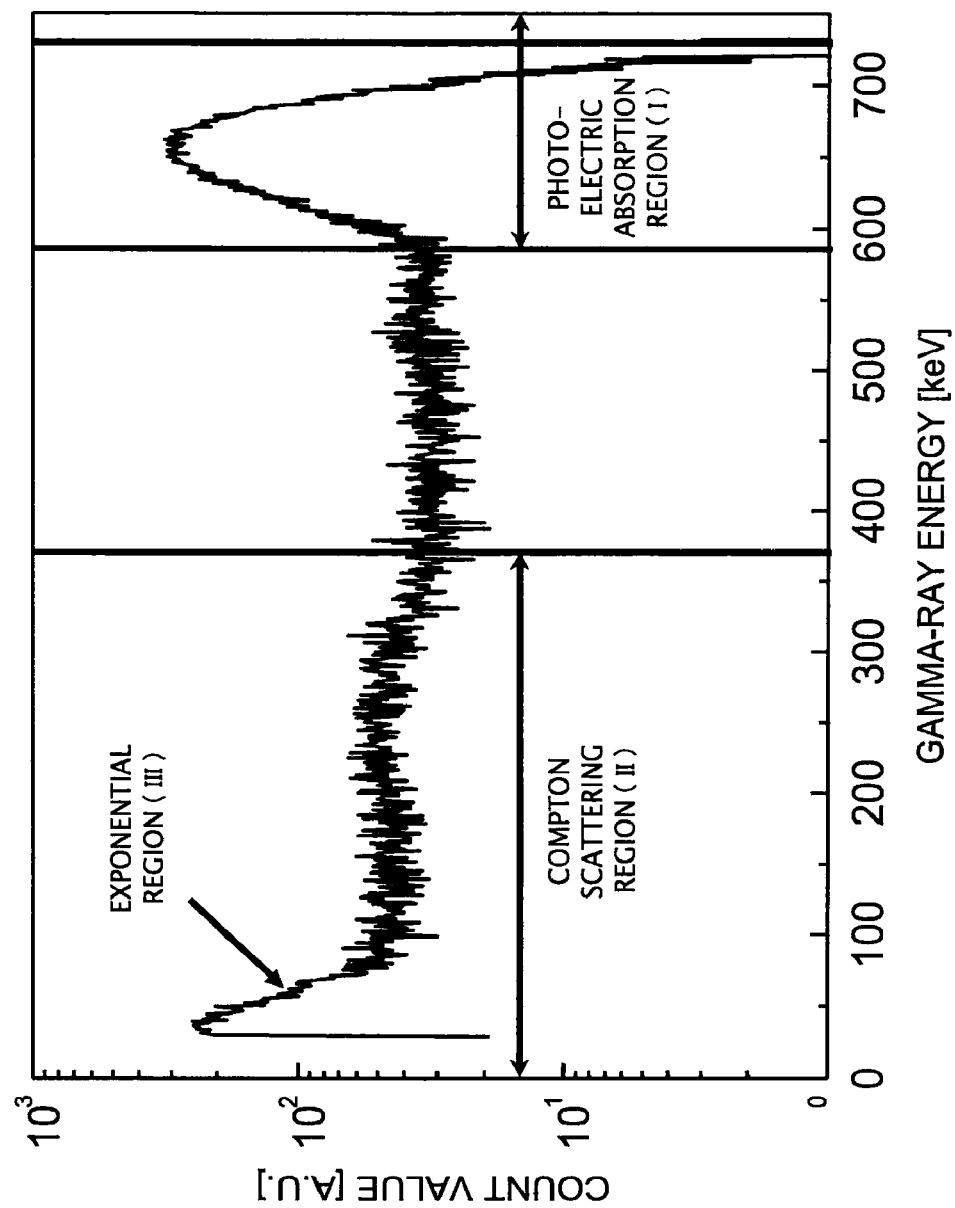
FIG. 2 is a diagram illustrating an energy spectrum of γ-rays with a BGO scintillation detector.

In general, when γ-rays are measured with an inorganic scintillator, a large absorption energy peak appears due to a photoelectric effect (region (I) in FIG. 2) and adsorption due to Compton scattering (region (II) in FIG. 2). FIG. 2 illustrates an energy spectrum of Cs-137 γ-rays (661.6 keV) with a BGO scintillation detector.

In the case of an organic scintillator, the energy peak due to the photoelectric effect as can be seen in the case of an inorganic scintillator does not appear, and only a spectrum due to Compton scattering is obtained.

Further, by employing the scintillator 10 having a size of 10 mm φ×10 mm or less, preferably 1 mm φ×2 mm or less, more preferably 1 mm φ×1 mm or less, it is possible to increase the probability that Compton scattering electrons generated in the scintillator 10 itself are dissipated from the scintillator 10. At this time, the region (I) will present a distribution which depends on the shape and size of the scintillator 10, rather than a linear distribution. When the shape is a micro sphere, the region (I) assumes a distribution which depends on an interaction cross section between the electron and the scintillator 10, which is generally an exponential distribution. Accordingly, with a combination of this region (I) with the region (III) which also varies exponentially, computation of a dosage by counting ionizing radiation can be achieved.

In particular, by setting the size of the scintillator 10 to 1 $mm^3$ or less, it is possible to increase the probability that the Compton scattering electrons generated in the scintillator 10 itself are dissipated from the scintillator 10 to thereby change the region (I) to an exponential distribution, with substantially no light emission generated due to the photoelectric effect within the substance.

The scintillator 10 is connected to an optical fiber 12 which transmits light that is converted from the ionizing radiation by the scintillator 10. It is also preferable that the optical fiber 12 is connected in a detachable manner by providing a connector in the middle thereof. This structure facilitates setting of the scintillator 10 at a desired position.

The optical fiber 12 is connected to a photoelectron multiplier tube 14. The photoelectron multiplier tube 14, which is a photoelectric converter, converts light (a light signal) supplied from the optical fiber 12 into an electric signal in accordance with the light intensity. A signal amplifier 16 is connected to the photoelectron multiplier tube 14 for amplifying the electric signal supplied from the photoelectron multiplier tube 14.

An output of the signal amplifier 16 is supplied to a discriminator 18, to which a threshold value is also input. The discriminator 18 discriminates, as an event, an electrical signal having a signal level which is a threshold value or greater, from other electrical signals input to the discriminator 18. Here, the discriminator 18 aims at finally discriminating an electrical signal used for detecting an accurate dosage from electrical noise, and may therefore determine in comparison with detection performed by a high performance ionization chamber when specific ionizing radiation is incident. The discriminator 18 can be formed of a comparator and the like.

In the present embodiment, it is assumed that the spectrum of adsorption energy in the scintillator 10 is represented by a pure exponential function, and if this assumption is established, no errors may be generated no matter what value is used for the threshold value. Actually, however, as it is considered that the absorption energy spectrum is not a perfect exponential function, some errors will be generated by setting a certain threshold value. Specifically, as the threshold value becomes higher, the range of estimation is increased, resulting in a possibility of a greater error. On the other hand, as the threshold value decreases, counting should be performed more than the necessary number of times, leading to a possibility that the measuring device is saturated with too many pulses. It is therefore preferable that the threshold value is set to an appropriate value in consideration of the above.

An output of the discriminator 18 is supplied to a counter 20, which counts the number of events discriminated by the discriminator 18.

The counting result obtained by the counter 20 is supplied to a computer 22 where the count value of events is converted to a dosage, which is then displayed on the display 24. The computer 22 executes a program which is directly stored in a recording medium such as a hard disk within the computer 22, to perform the processing which will be described below. Alternatively, the program may be directly written in the computer 22, may be loaded from a CD, or may be supplied to the computer 22 through a communication line.

The conversion from the count value of events to a dosage performed by the computer 22 will be described.

Assuming that when the energy applied to the scintillator 10 is E~E+dE, the number of events is $C_{Sc}(E)$, the dosage (energy) at the scintillator 10 is obtained by multiplying the event level with the energy of 0 to ∞ by the number of events, and is represented as follows:

[Formula 1]

$$D_{Sc}=\int_0^\infty EC_{Sc}(E)dE \qquad (1)$$

Figure 3:
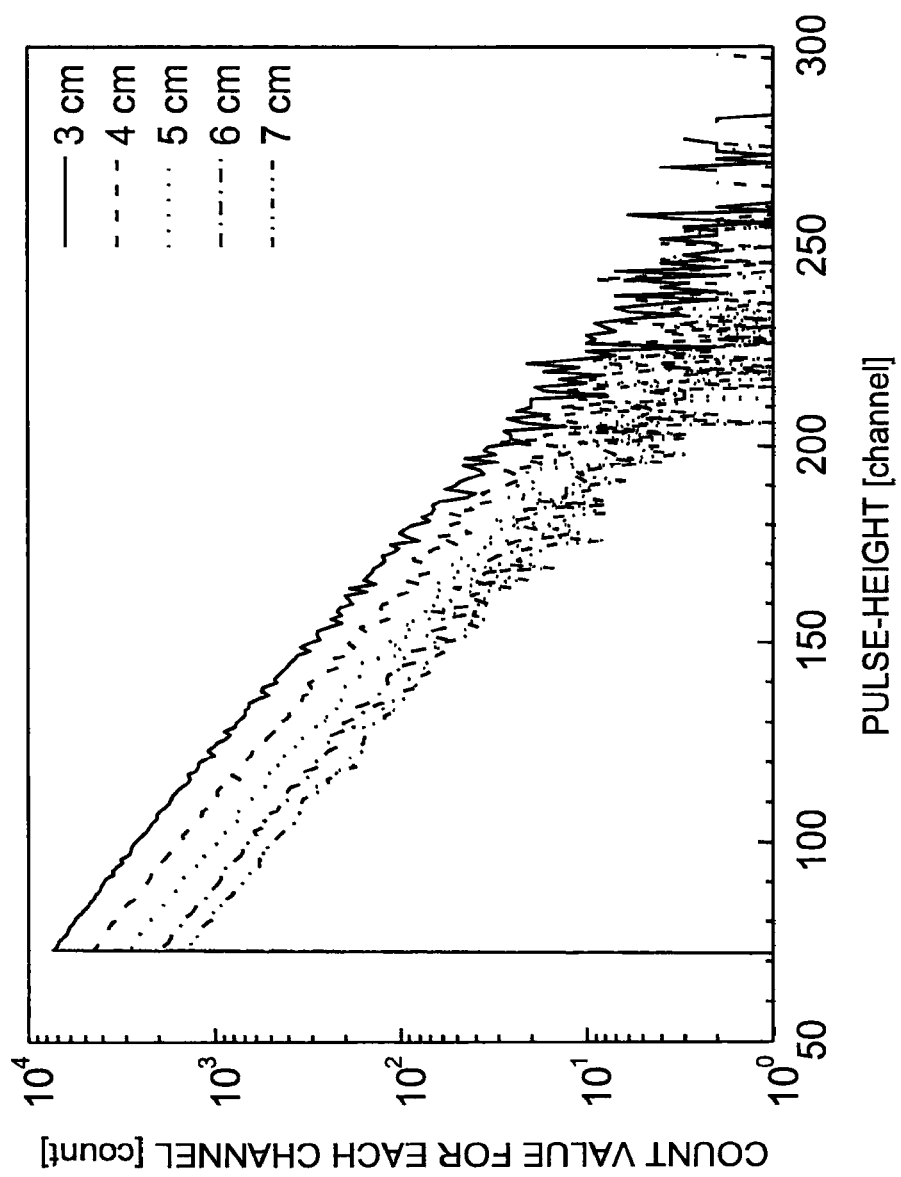
FIG. 3 is a diagram illustrating a pulse-height distribution spectrum with a supermicro plastic scintillator (BC490) with respect to an Ir-192 ray source in water.

As shown in FIG. 3, the pulse height spectrum (a count value for each pulse height channel) of a light emission event of a plastic scintillator with respect to Ir-192 γ-ray is a substantially exponential function. FIG. 3 illustrates results in a case where the distance to a ray source is shifted by 1 cm, from 3 cm to 7 cm. In each result, as the signal level (pulse height) of the light emission event becomes higher, the count value of the light emission event is exponentially decreased accordingly. Here, a plastic scintillator BC490 (manufactured by Saint-Gobain CDJ K.K.) is used as the scintillator 10.

Accordingly, the number of events $C_{Sc}(E)$ can be determined by the energy level and can be approximated as follows, provided that a measurement time is Δt:

[Formula 2]

$$C_{Sc}(E)=a\exp(-bE)\cdot\Delta t \qquad (2)$$

Here, "a" and "b" are constants defined based on the relationship shown in FIG. 3.

Consequently, the above formula (1) can be expressed as follows by using the above formula (2):

[Formula 3]

$$D_{Sc}=a\Delta t\int_0^\infty E\exp(-bE)dE \qquad (3)$$

On the other hand, application of energy by electrons with energy of $E_0$ or more, i.e. the total number of light emission events of the scintillator 10, is obtained by integration of the number of events $C_{Sc}(E)$ for each energy in the above formula (2) with respect to the energy $E_0$ or more, and can be represented as follows:

[Formula 4]

$$C_{total} = \int_{E_0}^{\infty} C_{Sc}(E)dE = a\Delta t \int_{E_0}^{\infty} \exp(-bE)dE \quad (4)$$

Here, the following formula (5) is known as a mathematical formula of integration by parts:

[Formula 5]

$$\int f(x)g'(x)dx = f(x)g(x) - \int f'(x)g(x)dx \quad (5)$$

In the above formula (5), assuming $f(x)=s$, $g(x)=\exp(-bx)$, the above formula (5) can be rewritten as follows:

[Formula 6]

$$\int x\{\exp(-bx)\}'dx = x\exp(-bx) - \int \{x\}' \exp(-bx)dx$$

By $$-b\int x\exp(-bx)dx = x\exp(-bx) - \int \exp(-bx)dx \quad (6)$$

application of the above formulas (3) and (4) to the formula (6), the following formula will be obtained:

[Formula 7]

$$-ab\int E\exp(-bE)dE = aE\exp(-bE) - a\int \exp(-bE)dE$$

$$-bD_{Sc} = [a\Delta t E \exp(-bE)]_0^\infty - (C_{total} + a\Delta t \int_0^{E_0} \exp(-bE)dE) \quad (7)$$

Accordingly, the dosage Ds, at the scintillator 10 can be represented as follows:

[Formula 8]

$$D_{Sc} = \frac{C_{total}}{b} - \frac{a\Delta t}{b^2}\{\exp(-bE_0) - 1\} \quad (8)$$

Further, the absorbed dose in water $D_W$ is obtained from the above formulas (1) and (8) as follows:

[Formula 9]

$$D_W = \frac{\left(\frac{\mu_{en}}{\rho}\right)_W}{\left(\frac{\mu_{en}}{\rho}\right)_{Sc}} \left[\frac{C_{total}}{b} - \frac{a\Delta t}{b^2}\{\exp(-bE_0) - 1\}\right] \quad (9)$$

In the above formula, $(\mu_{en}/\rho)$ [m²·kg⁻¹] represents a mass energy transfer coefficient, and such a coefficient with subscript "Sc" indicates that of the scintillator 10 and the coefficient with subscript "W" indicates that of water. More specifically, in the first term of the right side of the formula (9), the dosage in the scintillator 10 is converted to a water absorbed dose.

Here, provided that the following is defined:

[Formula 10]

$$\alpha = \frac{1}{b} \frac{\left(\frac{\mu_{en}}{\rho}\right)_W}{\left(\frac{\mu_{en}}{\rho}\right)_{Sc}}, \quad (10)$$

$$\beta = \left[\frac{a}{b}\{\exp(-bE_0) - 1\}\right]$$

the water absorbed dose $D_W$ is expressed as follows:

[Formula 11]

$$D_W = \alpha(C_{total} - \beta\Delta t) \quad (11)$$

Accordingly, when the correction coefficients α and β are determined, the water absorbed dose $D_W$ can be obtained from the total number of pulse counts $C_{total}$ and the measurement time Δt.

Figure 4:
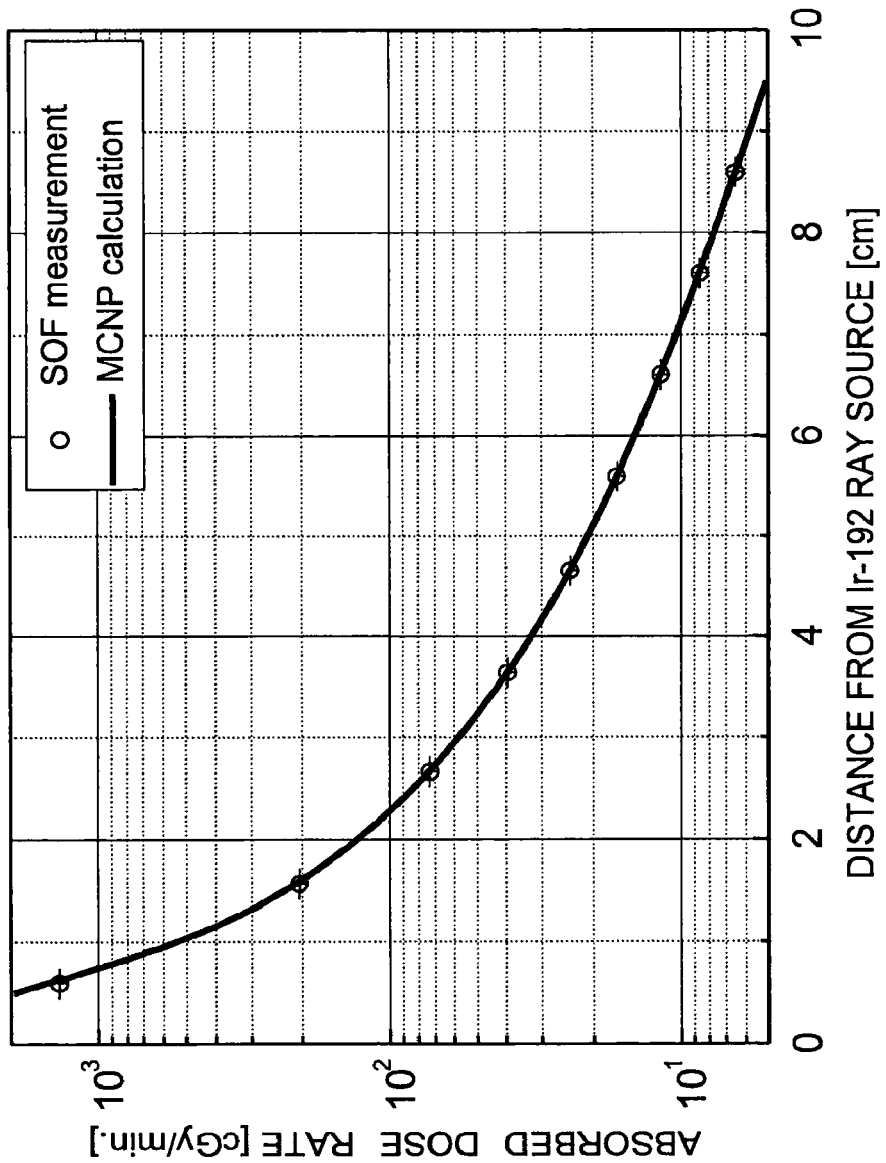
FIG. 4 is a diagram illustrating measurement results of dosage distribution with an Ir-192 ray source in water phantom.

FIG. 4 illustrates results of measuring a relationship (absorbed dose rate distribution) between a distance from a ray source and an absorbed dose rate ([cGy/min]) in water phantom in which an Ir-192 source for brachytherapy is employed, by using the device according to the present embodiment.

Here, the Monte Carlo N-Particle Transport Code (MCNP-4C) was used for comparison with the measurement results. As can be seen from FIG. 4, the measurement results which match the MCNP-4C code very precisely could be obtained with respect to changes in dosages over two digits or more. Also, such a measurement over a wide range as shown is one of the features of the present embodiment.

Figure 5:
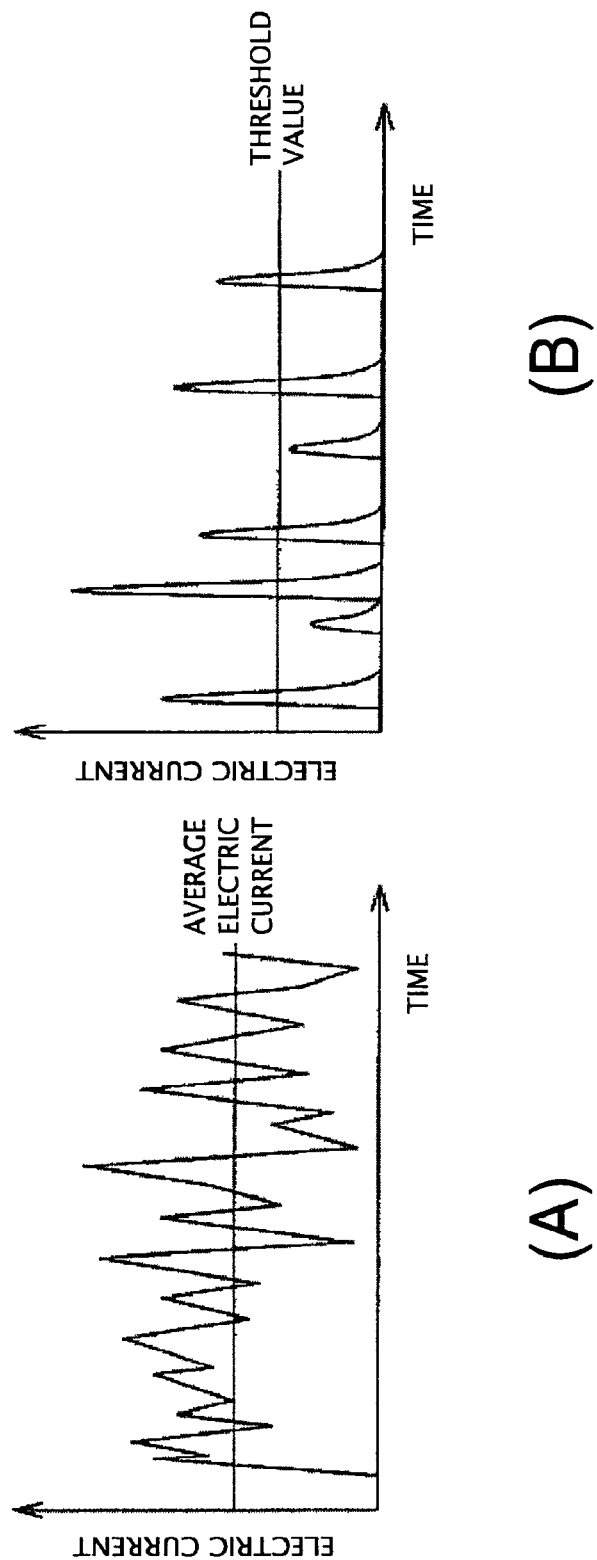
FIG. 5 is a diagram illustrating a comparison between a conventional detection method (A) and a detection method according to the embodiment (B)

FIG. 5 illustrates a comparison between the dosage measurement of the present embodiment and the conventional dosage measurement. As shown, while in the conventional technology integration of dosage is performed to detect the dosage as an average electric current amount, in the present embodiment, the dosage is obtained from the number of events equal to a threshold value or greater. With the method of the present embodiment, highly precise detection can be achieved in a relatively simple manner concerning the scintillator 10 and a processing circuit thereof.

Further, effects of the Cherenkov light on the measurement as described in the above-mentioned JP 2004-526155 A are also found in the present embodiment. However, the following measures can be taken to address this problem.

First, a plastic scintillator which emits green light (about 490 nm) is used as the scintillator 10. Here, the wavelength spectrum of the Cherenkov light expands to near the red light region (600 nm) depending on its intensity, and has a sufficient intensity even in the blue light region (about 420 nm). This nature is utilized to split light using a beam splitter which separates light, with the wavelength of 455 nm being used as a border, so that the Cherenkov light is determined when light of 455 nm or less and light of 455 nm or more is measured simultaneously and a signal is determined when only light of 455 nm or more is measured. Then, the Cherenkov light which is determined is excluded from events, so that the effects of Cherenkov light can be removed in a simple manner. Also, this method in which, contrary to the technology described in JP 2004-526155 A, a difference is not utilized, has an advantage that the SN ratio is high. While in this example, a scintillator which emits green light is used, removal of the Cherenkov light can be achieved using a similar principle when a scintillator which emits blue light is used.

Figure 6:
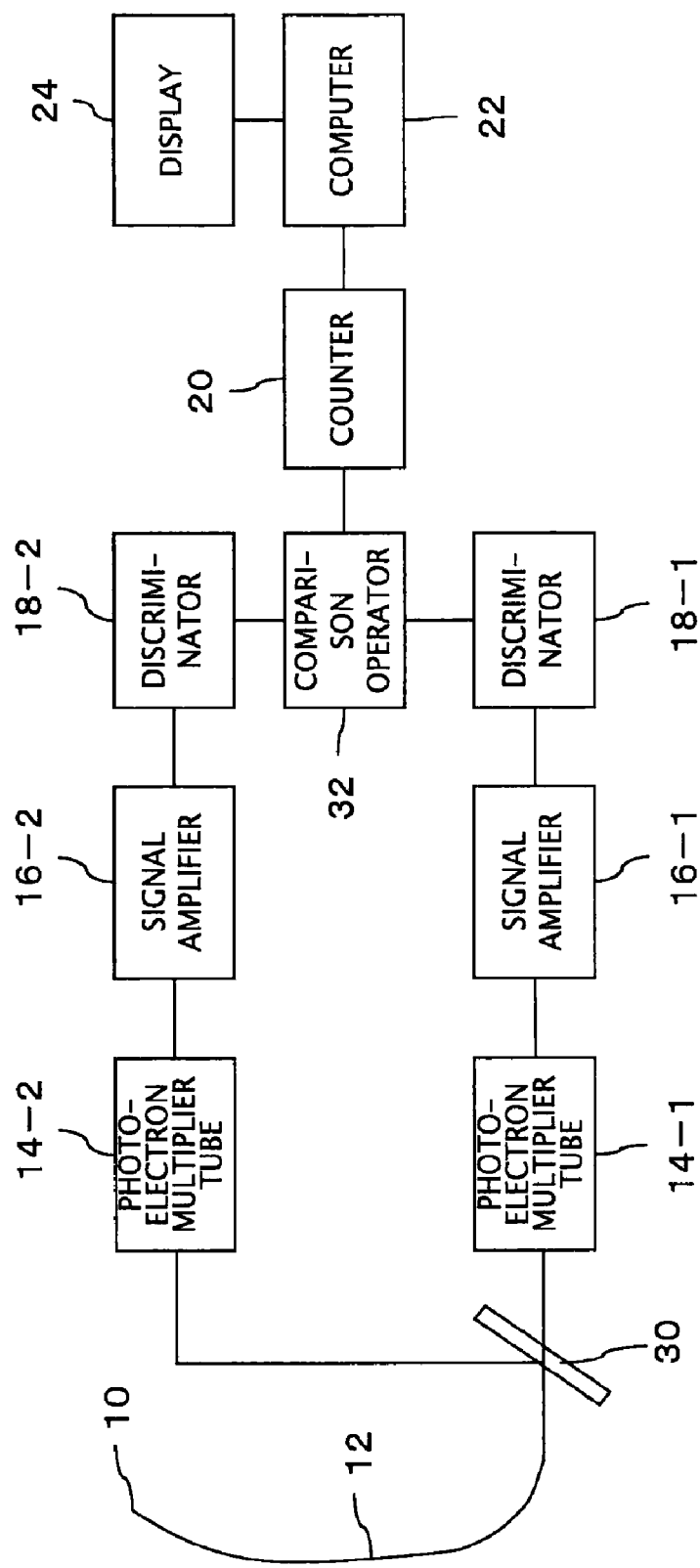
FIG. 6 is a diagram illustrating a structure according to another embodiment.

FIG. 6 illustrates an example structure for this case. Light emitted by the scintillator 10 is transmitted, via the optical fiber 12, to the beam splitter 30 where the light is divided into light of 455 nm or less and light of 455 nm or more. The light of 455 nm or less is directed to a photoelectron multiplier tube 14-1, a signal amplifier 16-1, and a discriminator 18-1, where an event is detected, and a signal concerning the event which is detected is supplied to a comparison operator 32. On the other hand, the light of 455 nm or more is directed to a photoelectron multiplier tube 14-2, a signal amplifier 16-2, and a discriminator 18-2, where an event is detected, and a signal concerning the event which is detected is supplied to the comparison operator 32.

Here, the comparison operator 32 is formed by an anti-coincidence counter circuit. More specifically, the comparison operator 32 outputs no count signals when signals are supplied from both discriminators 18-1 and 18-2 at the same timing and outputs a count signal only when a necessary signal is supplied. It is assumed, for example, that, of a blue light emission signal B and a green light emission signal G, the light emission signal G is necessary. When only the G signal is supplied to the comparison operator 32 without the B signal being supplied simultaneously, the comparison operator 32 outputs a count signal. When only the B signal is supplied to the comparison operator 32, without the G signal being supplied simultaneously, or when the B signal and the G signal are input simultaneously, the comparison operator 32 does not output a count signal. In other words, a gate is formed by the B signal to allow the G signal to pass only when B signal is not present. With this structure, the comparison operator 32, based on the signals supplied from the both discriminators 18-1 and 18-2, removes a signal of the Cherenkov light and outputs a count signal. Accordingly, the counter 20 can count the count signals supplied from the comparison operator 32, while eliminating the effects of the Cherenkov light.

Here, as the light of 455 nm or less and the light of 455 nm or more separated by the beam splitter 30 does not necessarily have the same level, it is preferable to adopt different threshold values for the discriminators 18-1 and 18-2, so that appropriate determination can be performed.

As described above, in the present embodiment, an amount of light emission at the scintillator 10 is converted to an electric current value (voltage value) by the photoelectron multiplier tube 14, and then the discriminator 18 is employed to discriminate only events with a threshold light emission amount or more, and the counter 20 further counts the number of events. In general, the photoelectron multiplier tube 14, the discriminator 18, and the counter 20 are inexpensive, and therefore the present embodiment does not require an expensive micro ammeter as required in JP 2004-526155 A.

Further, in the present embodiment, the scintillator 10 need not have a large size and a smaller scintillator is preferable. More specifically, with the use of a small scintillator 10, the spatial resolution concerning a measurement value can be increased. For example, while a scintillator of 1 mm $\phi \times 10$ mm is used in JP 2004-526155 A, a hemisphere scintillator having a diameter of about 1 mm, which is a scintillator about a thirtieth of the conventional scintillator, is used in the present embodiment. Consequently, the spatial resolution by measurement results is 20 times that of the conventional scintillator. It is therefore possible to detect and measure γ-rays within a living body and also to accurately measure the dosage during radiotherapy, which could only be measured based on vague estimation in the conventional technology.

Further, by increasing the probability that Compton scattering electrons generated by the scintillator itself are dissipated from the scintillator, an exponential distribution can be obtained, so that accurate detection of the radiation dose can be performed.

Also, because the structure of a device can be simplified as described above, it is easy to provide a multi-channel structure in which a large number of scintillators 10 are provided to detect the radiation doses at a large number of positions.

What is claimed is:

1. A radiation dosimeter, comprising:
a scintillator which emits light by incident ionizing radiation;
a photoelectric converter which converts light, which is an output of the scintillator, to an electric current;
a counter which counts the number of events, concerning an output from the photoelectric converter, having an intensity that is a predetermined threshold value or greater; and
a dosage computing unit which converts a count value obtained by the counter to a dosage to obtain the dosage, based on a relationship in which a frequency of occurrence of each event exponentially decreases as the intensity of light of the event increases.

2. The radiation dosimeter according to claim 1, wherein the scintillator is a plastic scintillator.

3. The radiation dosimeter according to claim 2, wherein the dosage computing unit computes a dosage $D_{Sc}$ in the scintillator based on the following formula:

$$D_{Sc}=(C_{total}/b)-(a\Delta t/b^2)\{\exp(-bE_0)-1\}$$

wherein a and b are constants, $C_{total}$ is a count number of events, $\Delta t$ is an event count time, and $E_0$ is the threshold value.

4. The radiation dosimeter according to claim 1, wherein the scintillator contains a light element as a major component and has an emission decay time of 10 nanosecond or less.

5. The radiation dosimeter according to claim 4, wherein the dosage computing unit computes a dosage $D_{Sc}$ in the scintillator based on the following formula:

$$D_{Sc}=(C_{total}/b)-(a\Delta t/b^2)\{\exp(-bE_0)-1\}$$

wherein a and b are constants, $C_{total}$ is a count number of events, $\Delta t$ is an event count time, and $E_0$ is the threshold value.

6. The radiation dosimeter according to claim 1, wherein a volume of the scintillator is 1 mm$^3$ or less.

7. The radiation dosimeter according to claim 6, wherein the dosage computing unit computes a dosage $D_{Sc}$ in the scintillator based on the following formula:

$$D_{Sc}=(C_{total}/b)-(a\Delta t/b^2)\{\exp(-bE_0)-1\}$$

wherein a and b are constants, $C_{total}$ is a count number of events, $\Delta t$ is an event count time, and $E_0$ is the threshold value.

8. The radiation dosimeter according to any one of claim 1, wherein
the dosage computing unit computes a dosage $D_{Sc}$ in the scintillator based on the following formula:

$$D_{Sc}=(C_{total}/b)-(a\Delta t/b^2)\{\exp(-bE_0)-1\}$$

wherein a and b are constants, $C_{total}$ is a count number of events, $\Delta t$ is an event count time, and $E_0$ is the threshold value.

9. The radiation dosimeter according to claim 1, wherein Cherenkov light and light emission by the scintillator are discriminated from each other based on whether light emission at a plurality of different wavelengths occurs simultaneously or only light emission at a single specific wavelength occurs, and counting is performed so that light emission other than light emission by the scintillator is excluded.

10. A radiation dose computing program for computing a dosage by a scintillator, the program causing a computer to execute a process comprising:
accepting a count value obtained by counting a number of events having an intensity of a predetermined threshold value or greater, concerning an electrical signal which is converted to an electric current from a light output from the scintillator which emits light by incident ionizing radiation; and
converting the count value which is accepted to a dosage based on a relationship in which a frequency of occurrence of each event exponentially decreases as the intensity of light of the event increases, thereby obtaining the dosage.

11. The radiation dose computing program according to claim 10, wherein
the relationship which is prestored is based on the following formula:

$$D_{Sc}=(C_{total}/b)-(a\Delta t/b^2)\{\exp(-bE_0)-1\}$$

wherein a and b are constants, $C_{total}$ is a count number of events, $\Delta t$ is an event count time, and $E_0$ is the threshold value.

12. A medium storing a radiation dose computing program for computing a dosage by a scintillator, the program causing a computer to execute a process comprising:
   accepting a count value obtained by counting a number of events having an intensity of a predetermined threshold value or greater, concerning an electrical signal which is converted to an electric current from a light output from the scintillator which emits light by incident ionizing radiation; and
   converting the count value which is accepted to a dosage based on a relationship in which a frequency of occurrence of each event exponentially decreases as the intensity of light of the event increases, thereby obtaining the dosage.

13. The medium storing a radiation dose computing program according to claim 12, wherein
the relationship which is prestored is based on the following formula:

$$D_{Sc}=(C_{total}/b)-(a\Delta t/b^2)\{\exp(-bE_0)-1\}$$

wherein a and b are constants, $C_{total}$ is a count number of events, $\Delta t$ is an event count time, and $E_0$ is the threshold value.

* * * * *